(12) United States Patent
Li et al.

(10) Patent No.: US 8,507,716 B2
(45) Date of Patent: Aug. 13, 2013

(54) PROCESS FOR PREPARING PEMETREXED DISODIUM AND ITS INTERMEDIATE, 4-(4-CARBOMETHOXYPHENYL) BUTANAL

(75) Inventors: Jinliang Li, Shanghai (CN); Nan Zhao, Shanghai (CN)

(73) Assignee: Shanghai Cdymax Pharmaceuticals Co., Ltd, Shanghai (CN)

( * ) Notice: Subject to any disclaimer, the term of this patent is extended or adjusted under 35 U.S.C. 154(b) by 234 days.

(21) Appl. No.: 12/995,257

(22) PCT Filed: Nov. 25, 2008

(86) PCT No.: PCT/CN2008/073182
§ 371 (c)(1),
(2), (4) Date: Jan. 25, 2011

(87) PCT Pub. No.: WO2009/143684
PCT Pub. Date: Dec. 3, 2009

(65) Prior Publication Data
US 2011/0124861 A1    May 26, 2011

(30) Foreign Application Priority Data
May 30, 2008    (CN) .......................... 2008 1 0038375

(51) Int. Cl.
*C07C 69/76*    (2006.01)
*C07C 69/95*    (2006.01)

(52) U.S. Cl.
USPC .......................................................... 560/51

(58) Field of Classification Search
None
See application file for complete search history.

(56) References Cited

U.S. PATENT DOCUMENTS
3,210,325 A * 10/1965 De Witt et al. ................. 526/250

FOREIGN PATENT DOCUMENTS
CN    1800169    7/2006
EP    0905128    3/1999

OTHER PUBLICATIONS

Introduction to Organic Laboratory Techniques: A Small Scale Approach (2005), p. 815.*
Synthesis of 4-(4-carbomethoxyphenyl)butanal; Chemistry Industry Times, 20(1) 2006, pp. 54-55. (English translation of Chinese document provided by Applicants).*
International Search Report; PCT/CN2008/073182; Mar. 5, 2009; Li Yong.
Taylor, et al; "A Convergent Synthesis of 5,10-Dideaza-5,6,7,8-tetrahydrofolic Acid and 5,10-Dideaza-5,6,7,8-tetrahydrohomofolic Acid. An Effective Principle for Carbonyl Group Activation;" J. Org. Chem. 1990, 55; pp. 3222-3227.
Larock, et al.; "Synthesis of Aryl-Substituted Aldehydes and Ketones Via Palladium-Catalyzed Coupling of Aryl halides and Non-Allylic Unsaturated Alcohols"; Tetrahedron Letters, vol. 30, No. 48, pp. 6629-6632, 1989.
Jianguang et al. "Synthesis of 4—(4—Carbomethoxyphenyl) butane", Chemistry Industry Times, vol. 20, No. 1, pp. 54-55 (Jan. 1, 2006).

* cited by examiner

*Primary Examiner* — Jeffrey Murray
(74) *Attorney, Agent, or Firm* — Fish & Richardson P.C.

(57) ABSTRACT

The present invention provides a process for preparing pemetrexed disodium and its intermediate, 4-(4-carbomethoxyphenyl)butanal. The process for preparing the intermediate comprises the following steps: condensing methyl 4-bromobenzoate with 3-buten-1-ol; extracting with an organic solvent during the work-up; adding silica gel to decolorize; and evaporating the organic solvent to give 4-(4-carbomethoxyphenyl)butanal. The product obtained by the present process, with a yield of higher than 80%, and a purity measured by GC of higher than 95%, may be directly used in the next bromination reaction for synthesizing pemetrexed disodium without purification. The present process is suitable for industrial production, as the operation is simple and the reagents used are cheap and readily available.

7 Claims, No Drawings

PROCESS FOR PREPARING PEMETREXED DISODIUM AND ITS INTERMEDIATE, 4-(4-CARBOMETHOXYPHENYL) BUTANAL

TECHNICAL FIELD

The present invention relates to the chemistry area, in particularly, to the process for preparing pemetrexed disodium and its intermediate, 4-(4-carbomethoxyphenyl)butanal.

BACKGROUND ART

The chemical name of pemetrexed disodium is N-{4-[2-(2-amino-4-oxo-4,7-dihydro-1H-pyrrolo[2,3-d]pyrimidin-5-yl)ethyl]benzoyl}-L-glutamic acid disodium salt, represented by the following formula:

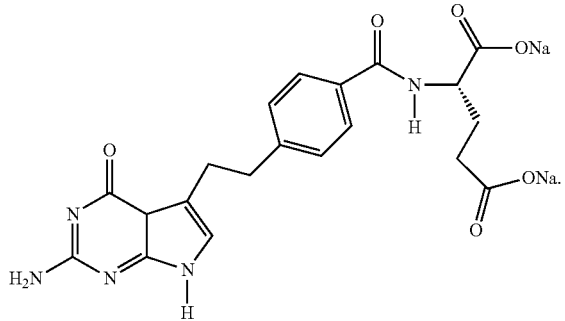

Pemetrexed disodium is an anti-tumor medicament against folic acid metabolism, which functions by interfering with folic acid-dependent metabolism process in the cell replication. As in vitro experiment demonstrates, pemetrexed disodium can inhibit folic acid-dependent enzymes, such as thymidylate synthetase, dihydrofolate reductase and glycineribonucleosideformyltransferase, which involve the biosynthesis of thymidine and purine nucleoside.

Currently, the commonly used process for preparing pemetrexed disodium is disclosed in EP 0905128. In the process disclosed, 4-(4-carbomethoxyphenyl)butanal is a key intermediate for preparing pemetrexed disodium.

Three processes for preparing 4-(4-carbomethoxyphenyl) butanal have been reported:

1. *J. Org. Chem.*, 1990, 55:3222-7 has reported that the intermediate can be obtained by condensing 3-butyn-1-ol with methyl p-bromobenzoate, hydrogenating with palladium carbon (Pd/C), and oxidizing the resulting alcohol by PCC. Such process is tedious and some reagents are expensive.

2. *Tetrahedron Letters*, 1989, 30:6629-32 has reported that the intermediate can be obtained by condensing 3-buten-1-ol with methyl p-bromobenzoate, and separating by column chromatography to obtain a pure product. Such process is not suitable for industrial production due to the use of column chromatography.

3. *Chemical Industry Times*, 2006, 20:54-55 has reported that the intermediate can be obtained by reacting the crude product of 4-(4-carbomethoxyphenyl)butanal obtained by condensing 3-buten-1-ol and methyl p-bromobenzoate with sodium bisulfite to provide a sulfonate salt, then treating the sulfonate salt with hydrochloric acid to produce a pure intermediate. The product obtained by such process is of high purity, however, the total yield is merely 38%.

Therefore, there is an urgent need in the art for improving the process for preparing 4-(4-carbomethoxyphenyl)butanal in order to prepare pemetrexed disodium more efficiently, and in a industrial-scale.

CONTENTS OF THE INVENTION

The object of the present invention is to provide a process for synthesis of 4-(4-carbomethoxyphenyl)butanal in order to overcome the shortcomings described above and facilitate an industrial production.

In the first aspect of the present invention, a process for synthesis of 4-(4-carbomethoxyphenyl)butanal is provided, comprising the following steps:
(a) condensing methyl p-bromobenzoate with 3-buten-1-ol to give a reaction mixture containing 4-(4-carbomethoxyphenyl)butanal;
(b) extracting the reaction mixture with an organic solvent to obtain an organic extract;
(c) decolorizing the organic extract with silica gel, then removing the organic solvent to give 4-(4-carbomethoxyphenyl) butanal.

In another preferred embodiment, the organic solvent is selected from: (i) one or more of C5-C8 alkane, petroleum ether and C2-C4 ether; (ii) a solvent mixture of the solvent in (i) and ethyl acetate; (iii) ethyl acetate.

In another preferred embodiment, the C5-C8 alkane is selected from n-hexane or cyclohexane, and C2-C4 ether is selected from isopropyl ether.

In another preferred embodiment, the organic solvent is selected from a mixture of n-hexane or cyclohexane and ethyl acetate, with the volume ratio being 4~8:1.

In another preferred embodiment, step (a) comprises adding water to quench the reaction and obtain a reaction mixture; step (c) comprises adjusting the pH of the organic extract to pH of 7-8 by using a solution of sodium bicarbonate, and washing the organic extract water, and then decolorizing with silica gel.

In another preferred embodiment, in step (c), the organic solvent is removed by evaporation under reduced pressure or vacuum drying.

In another preferred embodiment, the weight concentration of the sodium bicarbonate solution is 1% to a saturated solution. The sodium bicarbonate solution is a saturated sodium bicarbonate solution.

In another preferred embodiment, in step (b), the volume ratio of the reaction mixture containing 4-(4-carbomethoxyphenyl)butanal to the organic solvent is 1:0.1~1, preferably 1:0.15~0.50.

In the second aspect of the present invention, a process for synthesis of pemetrexed disodium is provided, comprising the following steps:
(a) condensing methyl p-bromobenzoate with 3-buten-1-ol to give a reaction mixture containing 4-(4-carbomethoxyphenyl)butanal;
(b) extracting the reaction mixture with an organic solvent to obtain an organic extract;
(c) decolorizing the organic extract with silica gel, then removing the organic solvent to give 4-(4-carbomethoxyphenyl)butanal;
(d) performing a bromiantion reaction between 4-(4-carbomethoxyphenyl)butanal and $Br_2$ to give 2-bromo-4-(4-carbomethoxyphenyl)butanal;
(e) reacting 2-bromo-4-(4-carbomethoxyphenyl)butanal with 2,4-diamino-6-hydroxypyrimidine to give methyl 4-[2-(2-amino-4,7-dihydro-4-oxo-1H-pyrrolo[2,3-d]pyrimidin-5-yl)ethyl]benzoate;

(f) hydrolyzing methyl 4-[2-(2-amino-4,7-dihydro-4-oxo-1H-pyrrolo[2,3-d]pyrimidin-5-yl)ethyl]benzoate to give 4-[2-(2-amino-4,7-dihydro-4-oxo-1H-pyrrolo[2,3-d]pyrimidin-5-yl)ethyl]benzoic acid;

(g) condensing 4-[2-(2-amino-4,7-dihydro-4-oxo-1H-pyrrolo[2,3-d]pyrimidin-5-yl)ethyl]benzoic acid with diethyl L-glutamate hydrochlorate to give N-[4-[2-(2-amino-4,7-dihydro-4-oxo-1H-pyrrolo[2,3-d]pyrimidin-5-yl)ethyl]benzoyl-L-glutamic acid diethyl ester, and then forming a p-toluenesulfonate salt thereof; and (h) reacting N-[4-[2-(2-amino-4,7-dihydro-4-oxo-1H-pyrrolo[2,3-d]pyrimidin-5-yl)ethyl]benzoyl-L-glutamic acid diethyl ester p-toluenesulfonate salt with sodium hydroxide to give pemetrexed disodium.

In the third aspect of the present invention, an improved process for preparing pemetrexed disodium is provided, wherein the intermediate, 4-(4-carbomethoxyphenyl)butanal, is prepared by the process described in the first aspect of the present invention.

DETAILED DESCRIPTION OF THE INVENTION

Through extensive and intensive investigations, the present inventors found for the first time that from the reaction mixture resulted from condensing methyl bromobenzoate with 3-buten-1-ol, 4-(4-carbomethoxyphenyl)butanal of high purity could be efficiently obtained through extraction with organic solvent, decoloration with silica gel, and removing the organic solvent. The intermediate could be used directly to the next bromination step for preparing pemetrexed disodium without further purification. The present invention was made based on the above findings.

The process of the invention includes the following steps:
condensing methyl p-bromobenzoate with 3-buten-1-ol; extracting the reaction mixture with an organic solvent to obtain an organic extract; decolorizing the organic extract with silica gel, and then removing the organic solvent to give 4-(4-carbomethoxyphenyl) butanal.

In a preferred embodiment, the process of the present process comprises the following steps:

(a) dissolving methyl p-bromobenzoate in a suitable solvent (a solvent of high polarity such as DMF, DMA or DMSO); adding lithium acetate dihydrate; lithium chloride and tetrabutyl ammonium bromide to the solution; bubbling nitrogen; adding 3-buten-1-ol and palladium acetate to undergo a condensation reaction; then adding water to quench the reaction, thereby giving a reaction mixture;

(b) extracting the reaction mixture with an organic solvent to give an organic phase (an extract);

(c) adjusting the pH to 7~8 using a solution of sodium bicarbonate, washing the organic phase with water, adding silica gel to decolorize the organic phase, and removing the organic solvent by evaporation under reduced pressure, thereby giving the product.

In the process of the present invention, the organic solvent is selected from:

(i) one or more of C5-C8 alkane, petroleum ether and C2-C4 ether; or (ii) a solvent mixture of the solvent in (i) and ethyl acetate. Preferably, the C5-C8 alkane is n-hexane or cyclohexane, and C2-C4 ether is isopropyl ether.

The solvent mixture of n-hexane (or cyclohexane) and ethyl acetate is preferred. The volume ratio of n-hexane (or cyclohexane) to ethyl acetate in the mixture is not particularly limited, generally being 4~8:1.

The weight concentration of the sodium bicarbonate solution is 1% to a saturated solution, with the saturated sodium bicarbonate solution being preferred.

Preferably, the volume ratio of the reaction mixture (an aqueous solution) to the organic solvent in step (b) is 1:0.1~1, with 0.15~0.50 being preferred.

The product yield obtained by the process of the present invention can be up to over 80%, and the purity can be up to over 95% detected by GC, and the product can be used directly in the next bromination reaction for synthesizing pemetrexed disodium without further purification.

Additionally, the present invention also provides an improved process for synthesizing pemetrexed disodium, wherein the intermediate, 4-(4-carbomethoxyphenyl)butanal, is prepared according to the above process of the present invention. In other words, the intermediate, 4-(4-carbomethoxyphenyl)butanal obtained by the process of the present invention can be used to prepare pemetrexed disodium according to the routine method in the prior art.

A preferable process for preparing pemetrexed disodium has been disclosed in EP 0905128, represented by the following scheme:

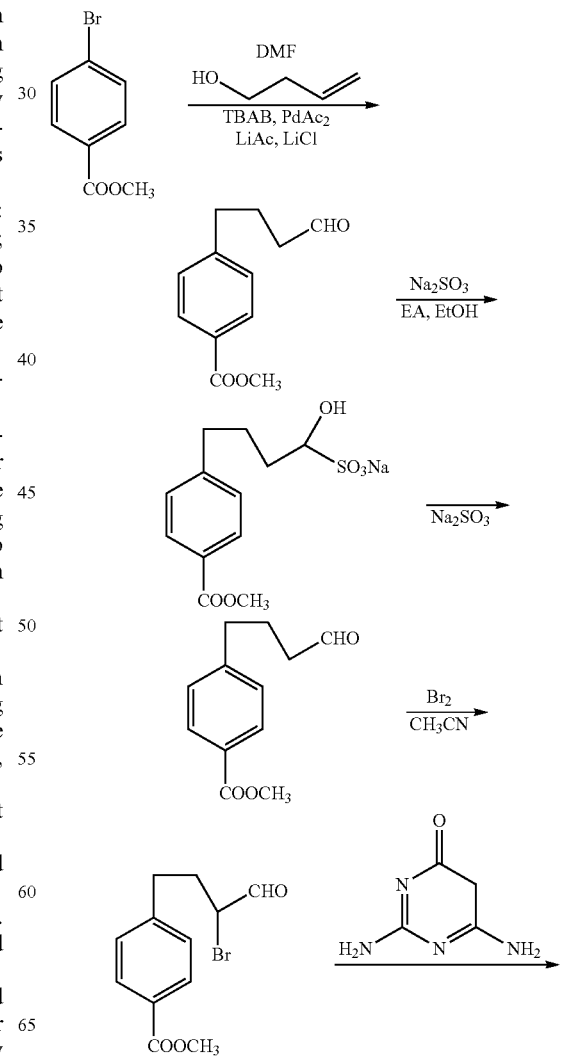

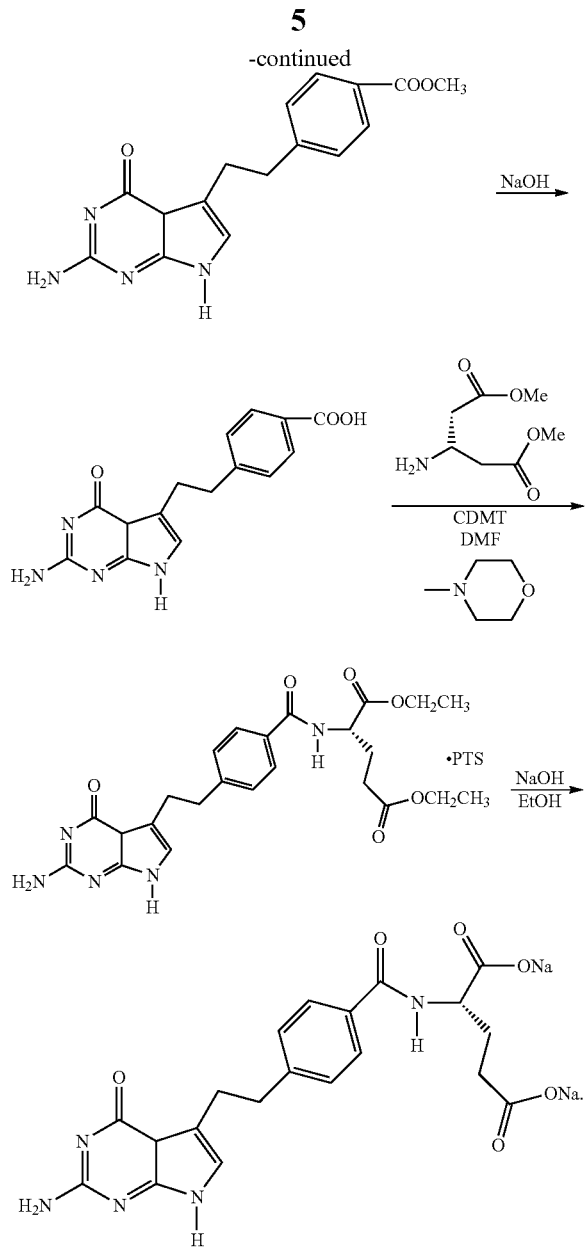

The intermediate, 4-(4-carbomethoxyphenyl)butanal obtained according to the present invention can be used directly in the bromination reaction in the above scheme without further purification.

The process according to the present invention for preparing the intermediate is simple in operation, and the reagents used are inexpensive and readily available, thus suitable for industrial production.

The Preferred Embodiments For Carrying Out The Invention

The invention is further illustrated by the following examples. It is appreciated that these examples are only intended to illustrate the invention, but not to limit the scope of the invention. For the experimental methods in the following examples, they are performed under routine conditions, or as instructed by the manufacturers, unless otherwise specified. Unless specified otherwise, all of the percent and parts are based on weight.

EXAMPLE 1

The preparation of 4-(4-carbomethoxyphenyl)butanal

Condensation reaction: methyl p-bromobenzoate (85.0 g, 0.395 mol) was dissolved in 1 L of DMF. To the solution were added 45.0 g of lithium acetate dihydrate, 50.0 g of lithium chloride and 60.0 g of tetrabutyl ammonium bromide. Nitrogen was bubbled through for 5 minutes. Then, 3-buten-1-ol (34.0 g, 0.472 mol) and 2.3 g of palladium acetate were added. The reaction mixture was stirred at 60 for 10 hours.

Separation: The reaction mixture was cooled to 25 and 1 L of water was added. The resulting mixture was extracted with 300 ml of a mixed solution of cyclohexane and ethyl acetate (6:1) for 3 times. The organic layers were combined and the pH of the combined organic layer was adjusted to 8 with a saturated sodium bicarbonate solution, and then washed with water (4×500 ml). To the organic layer was added 80 g of silica gel, and the resulting mixture was stirred for half an hour to be decolorized, and then filtered. The light yellow solution obtained was evaporated under reduced pressure at 40 to dryness to give 4-(4-carbomethoxyphenyl)butanal (70.0 g, 86.0% yield), with a purity of 96.3% detected by GC.

EXAMPLE 2

The preparation of 4-(4-carbomethoxyphenyl)butanal

Condensation reaction: methyl p-bromobenzoate (10.8 g, 0.050 mol) was dissolved in 150 mL of DMF. To the solution were added 5.7 g of lithium acetate dihydrate, 6.4 g of lithium chloride and 7.6 g of tetrabutyl ammonium bromide. The nitrogen was bubbled through for 5 minutes. Then, 3-buten-1-ol (4.3 g, 0.060 mol) and 0.3 g of palladium acetate were added. The reaction mixture was stirred at 60 for 10 hours.

Separation: The reaction mixture was cooled to 25 and 200 mL of water was added. The resulting mixture was extracted with 100 ml of a mixed solution of petroleum ether (60~90) and ethyl acetate (7:1) for 3 times. The organic layers were combined and the pH of the combined organic layer was adjusted to 7 with a saturated sodium bicarbonate solution, and then washed with water (5×50 ml). To the organic layer was added 10 g of silica gel, and the resulting mixture was stirred for half an hour to be decolorized. The light yellow solution obtained was evaporated under reduced pressure at 40 to dryness to give 4-(4-carbomethoxyphenyl)butanal (8.4 g, 81.6% yield), with a purity of 96.1% detected by GC.

EXAMPLE 3

The preparation of 4-(4-carbomethoxyphenyl)butanal

Condensation reaction: methyl p-bromobenzoate (10.8 g, 0.050 mol) was dissolved in 150 mL of DMF. To the solution were added 5.7 g of lithium acetate dihydrate, 6.4 g of lithium chloride and 7.6 g of tetrabutyl ammonium bromide. The nitrogen was bubbled through for 5 minutes. Then, 3-buten-1-ol (4.3 g, 0.060 mol) and 0.3 g of palladium acetate were added. The reaction mixture was stirred at 60 for 10 hours.

Separation: The reaction mixture was cooled to 25 and 200 mL of water was added. The resulting mixture was extracted with 100 ml of a mixed solution of isopropyl ether and ethyl acetate (9:1) for 3 times. The organic layers were combined and the pH of the combined organic layer was adjusted to 7.5 with a saturated sodium bicarbonate solution, and then washed with water (5×50 ml). To the organic layer was added 10 g of silica gel, and the resulting mixture was stirred for half an hour to be decolorized. The light yellow solution obtained was evaporated under reduced pressure at 40 to dryness to give 4-(4-carbomethoxyphenyl)butanal (8.0 g, 77.7% yield), with a purity of 95.2% detected by GC.

EXAMPLE 4

The preparation of
4-(4-carbomethoxyphenyl)butanal

Condensation reaction: methyl p-bromobenzoate (10.8 g, 0.050 mol) was dissolved in 150 mL of DMF. To the solution were added 5.7 g of lithium acetate dihydrate, 6.4 g of lithium chloride and 7.6 g of tetrabutyl ammonium bromide. The nitrogen was bubbled through for 5 minutes. Then, 3-buten-1-ol (4.3 g, 0.060 mol) and 0.3 g of palladium acetate were added. The reaction mixture was stirred at 60 for 10 hours.

Separation: The reaction mixture was cooled to 25 and 200 mL of water was added. The resulting mixture was extracted with 100 ml of a mixed solution of n-hexane and ethyl acetate (4:1) for 3 times. The organic layers were combined and the pH of the combined organic layer was adjusted to 7.6 with 5% sodium bicarbonate solution, and then washed with water (5×50 ml). To the organic layer was added 10 g of silica gel, and the resulting mixture was stirred for half an hour to be decolorized. The light yellow solution obtained was evaporated under reduced pressure at 40 to dryness to give 4-(4-carbomethoxyphenyl)butanal (8.2 g, 79.6% yield), with a purity of 95.0% detected by GC.

EXAMPLE 5

The preparation of
4-(4-carbomethoxyphenyl)butanal

Condensation reaction: methyl p-bromobenzoate (10.8 g, 0.050 mol) was dissolved in 150 mL of DMF. To the solution were added 5.7 g of lithium acetate dihydrate, 6.4 g of lithium chloride and 7.6 g of tetrabutyl ammonium bromide. The nitrogen was bubbled through for 5 minutes. Then, 3-buten-1-ol (4.3 g, 0.060 mol) and 0.3 g of palladium acetate were added. The reaction mixture was stirred at 60 for 10 hours.

Separation: The reaction mixture was cooled to 25 and 200 mL of water was added. The resulting mixture was extracted with 120 ml of a mixed solution of n-hexane and ethyl acetate (8:1) for 3 times. The organic layers were combined and the pH of the combined organic layer was adjusted to 7 with 2% sodium bicarbonate solution, and then washed with water (5×50 ml). To the organic layer was added 10 g of silica gel, and the resulting mixture was stirred for half an hour to be decolorized. The light yellow solution obtained was evaporated under reduced pressure at 40 to dryness to give 4-(4-carbomethoxyphenyl)butanal (7.6 g, 73.8% yield), with a purity of 96.5% detected by GC.

EXAMPLE 6

The preparation of
4-(4-carbomethoxyphenyl)butanal

Condensation reaction: methyl p-bromobenzoate (10.8 g, 0.050 mol) was dissolved in 150 mL of DMF. To the solution were added 5.7 g of lithium acetate dihydrate, 6.4 g of lithium chloride and 7.6 g of tetrabutyl ammonium bromide. The nitrogen was bubbled for 5 minutes. Then, 3-buten-1-ol (4.3 g, 0.060 mol) and 0.3 g of palladium acetate were added. The reaction mixture was stirred at 60 for 10 hours.

Separation: The reaction mixture was cooled to 20 and 200 mL of water was added. The resulting mixture was extracted with 100 ml of cyclohexane for 3 times. The organic layers were combined and the pH of the combined organic layer was adjusted to 7~8 with a saturated sodium bicarbonate solution, then washed with water (5×50 ml). To the organic layer was added 10 g of silica gel, and the resulting mixture was stirred for half an hour to be decolorized. The light yellow solution obtained was evaporated under reduced pressure at 40 to dryness to give 4-(4-carbomethoxyphenyl)butanal (5.4 g, 52.4% yield), with a purity of 96.8% detected by GC.

EXAMPLE 7

The preparation of
4-(4-carbomethoxyphenyl)butanal

Condensation reaction: methyl p-bromobenzoate (10.8 g, 0.050 mol) was dissolved in 150 mL of DMF. To the solution were added 5.7 g of lithium acetate dihydrate, 6.4 g of lithium chloride and 7.6 g of tetrabutyl ammonium bromide. The nitrogen was bubbled for 5 minutes. Then, 3-buten-1-ol (4.3 g, 0.060 mol) and 0.3 g of palladium acetate were added. The reaction mixture was stirred at 60 for 10 hours.

Separation: The reaction mixture was cooled to 25 and 200 mL of water was added. The resulting mixture was extracted with 120 ml of ethyl acetate for 3 times. The organic layers were combined and the pH of the combined organic layer was adjusted to 8 with a saturated sodium bicarbonate solution, and then washed with water (5×50 ml). To the organic layer was added 10 g of silica gel, and the resulting mixture was stirred for half an hour to be decolorized. The light yellow solution obtained was evaporated under reduced pressure at 40 to dryness to give 4-(4-carbomethoxyphenyl)butanal (9.0 g, 87.4% yield), with a purity of 81.6% detected by GC.

EXAMPLE 8

Next reaction example:

Methyl 4-[2-(2-amino-4,7-dihydro-4-oxo-1H-pyrrolo[2,3-d]pyrimidin-5-yl)ethyl]benzoate 4-(4-carbomethoxyphenyl) butanal (18.9 g) from Example 1 was added to acetonitrile (100 ml). The resulting solution was cooled to 0° C. with an ice bath, and $Br_2$ (4.72 ml) was added dropwise at 0° C. After the addition, the ice bath was removed, and the reaction was stirred at room temperature for 2 h. The reaction was evaporated under reduced pressure at room temperature for 20 minutes using a rotary evaporator. To the residue was added water (100 ml), 2,4-diamino-6-hydroxypyrimidine (12.3 g) and anhydrous sodium acetate (30.0 g). Then the nitrogen was bubbled for 5 minutes. The reaction was performed at 45 over night under $N_2$. After the reaction was completed, the reaction was cooled to and crystallized. The reaction was filtered to give an earthy yellow solid (wet weight: about 26.2 g).

4-[2-(2-amino-4,7-dihydro-4-oxo-1H-pyrrolo[2,3-d]pyrimidin-5-yl)ethyl]benzoic acid The above product (26.2 g) was added to a 2 N aqueous sodium hydroxide solution (310 ml), and the reaction mixture was stirred at 40 for 2 h. To the reaction mixture was added ethanol (460 ml). The pH of the solution was adjusted to 3~4 with 6 N hydrochloric acid with an ice/water bath, and a large amount of solid precipitated. The solid was filtered off, washed with 1:1 mixture of ethanol:water, and then dried to give a light yellow solid (18.8 g, 75.3% yield).

N-[4-[2-(2-amino-4,7-dihydro-4-oxo-1H-pyrrolo[2,3-d]pyrimidin-5-yl)ethyl]benzoyl-L-glutamic acid diethyl ester p-toluenesulfonate salt The above product (18.8 g) was suspended in DMF (150 ml). The mixture was stirred for 15 minutes, then N-methylmorpholine (19.0 g) was added. 2-chloro-4,6-dimethoxy-1,3,5-triazine (CDMT, 14.3 g) was added with an ice/water bath. The ice/water bath was removed, and the reaction mixture was stirred at room temperature for 40 minutes. Diethyl L-glutamate hydrochloride (19.5 g) was added and the reaction was further stirred for 2 h at 35. After the reaction was completed, to the reaction mixture was added dichloromethane (350 ml) and deionized water (350 ml), stirred for 15 minutes, and then the resulting mixture was allowed to separate, and the organic later was separated. The dichloromethane was evaporated under reduced pressure at 45 and ethanol was added to a total volume of 600 ml. The solution was heated to 70~75, then a solution of p-toluenesulfonic acid (30.8 g) in ethanol (500 ml) was added dropwise over 1 h, and a large amount of solid precipitated. The reaction mixture was refluxed continuously for 2 h, and then cooled to room temperature. The mixture was filtered and the filter cake was washed with anhydrous ethanol (750 ml), and then dried to give the off-white product (15.2 g).

N-[4-[2-(2-amino-4,7-dihydro-4-oxo-1H-pyrrolo[2,3-d]pyrimidin-5-yl)ethyl]benzoyl-L-glutamic acid disodium salt (pemetrexed disodium)

The above product (15.2 g) was dissolved in 1 N aqueous sodium hydroxide solution (90 ml) under nitrogen atmosphere with an ice bath. The mixture was stirred until the solid was completely dissolved. The pH of the solution was adjusted to 3 using 2 N hydrochloric acid with an ice bath, and a large amount of white solid precipitated. The solid was subjected to sucking filtration and drying and to the resulting solid was added dropwise 1 N aqueous sodium hydroxide solution while stirred until all the solid was just dissolved (at that time, the pH of the solution was 7.5~8.5). To the solution was added ethanol (150 ml). The slurry was filtered, and ethanol (400 ml) was added to the filtrate, which was kept in refrigerator over night, and a large amount of white crystal appeared. The crystal was filtered and dried to give N-[4-[2-(2-amino-4,7-dihydro-4-oxo-1H-pyrrolo[2,3-d]pyrimidin-5-yl)ethyl]benzoyl-L-glutamic acid disodium salt (9.9 g). The product was detected by $^1$H NMR and $^{13}$C NMR, and the result was consistent with EP 0905128.

It would be appreciated that, in the above teaching of invention, the skilled in the art could make a variety of changes or modifications to the invention, and these equivalents would still be within the scope of the invention defined by the appended claims of the application.

The invention claimed is:

1. A process for preparing 4-(4-carbomethoxyphenyl)butanal, comprising the following steps: (a) condensing methyl p-bromobenzoate with 3-buten-1-ol to give a reaction mixture containing 4-(4-carbomethoxyphenyl)butanal; (b) extracting the reaction mixture with an organic solvent to obtain an organic extract; (c) decolorizing the organic extract with silica gel, then removing the organic solvent to give 4-(4-carbomethoxyphenyl) butanal,
    wherein the organic solvent is selected from: (i) one or more of C5-C8 alkane, petroleum ether, and C2-C4 ether; (ii) a solvent mixture of the solvent in (i) and ethyl acetate; or (iii) ethyl acetate, and
    wherein the C5-C8 alkane is selected from n-hexane or cyclohexane, and C2-C4 ether is selected from isopropyl ether.

2. The process according to claim 1, wherein the organic solvent is selected from a mixture of n-hexane or cyclohexane and ethyl acetate, with the volume ratio of n-hexane or cyclohexane to ethyl acetate being 4:1 to 8:1.

3. The process according to claim 1, wherein step (a) comprises adding water to quench the reaction and obtain the reaction mixture; and step (c) comprises adjusting the pH of the organic extract to a pH of 7-8 by using a solution of sodium bicarbonate, and washing the organic extract with water, and then decolorizing with silica gel.

4. The process according to claim 1, wherein in step (c), the organic solvent is removed by evaporation under reduced pressure or vacuum drying.

5. The process according to claim 3, wherein weight concentration of the sodium bicarbonate solution is 1% to a saturated solution, with the saturated sodium bicarbonate solution being preferred.

6. The process according to claim 1, wherein in step (b), the volume ratio of the reaction mixture containing 4-(4-carbomethoxyphenyl)butanal to the organic solvent is 1:0.1 to 1:1.

7. The process according to claim 6, wherein in step (b), the volume ratio of the reaction mixture containing 4-(4-carbomethoxyphenyl)butanal to the organic solvent is 1:0.15 to 1:0.50.

* * * * *